(12) United States Patent
Kaiser

(10) Patent No.: US 7,256,051 B2
(45) Date of Patent: Aug. 14, 2007

(54) METHOD AND DEVICE FOR IDENTIFYING A MARKER USING A DETECTOR SUBSTANCE

(75) Inventor: Joachim Kaiser, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 651 days.

(21) Appl. No.: 10/398,227

(22) PCT Filed: Jul. 22, 2002

(86) PCT No.: PCT/DE02/02691

§ 371 (c)(1),
(2), (4) Date: Apr. 3, 2003

(87) PCT Pub. No.: WO03/015009

PCT Pub. Date: Feb. 20, 2003

(65) Prior Publication Data

US 2004/0035938 A1     Feb. 26, 2004

(30) Foreign Application Priority Data

Aug. 3, 2001   (DE) ................................ 101 37 484

(51) Int. Cl.
*G01N 21/76* (2006.01)
*G01N 33/02* (2006.01)
*G01N 33/543* (2006.01)
*G01N 21/86* (2006.01)
*G01D 18/00* (2006.01)
*G06K 9/74* (2006.01)

(52) U.S. Cl. ..................... 436/172; 436/20; 436/172; 436/518; 702/85; 356/71; 250/559.29

(58) Field of Classification Search ................ 436/172, 436/20, 518; 235/462
See application file for complete search history.

(56) References Cited

U.S. PATENT DOCUMENTS

| 3,716,699 | A | * | 2/1973 | Eckert et al. | .......... 235/462.17 |
| 4,983,817 | A | | 1/1991 | Dolash et al. | |
| 5,331,140 | A | | 7/1994 | Stephany | |
| 5,631,170 | A | * | 5/1997 | Attridge | ..................... 436/518 |
| 5,721,435 | A | * | 2/1998 | Troll | ..................... 250/559.29 |
| 5,753,511 | A | * | 5/1998 | Selinfreund | ................... 436/20 |
| 6,119,071 | A | * | 9/2000 | Gorenflo et al. | .............. 702/85 |
| 6,490,030 | B1 | * | 12/2002 | Gill et al. | ..................... 356/71 |
| 7,079,230 | B1 | * | 7/2006 | McInerney et al. | ........... 356/71 |

FOREIGN PATENT DOCUMENTS

| DE | 199 58 048 | 6/2001 |
| JP | 11306276 | 11/1999 |
| WO | 9750053 | 12/1997 |
| WO | 9800806 | 1/1998 |
| WO | 9947702 | 9/1999 |

* cited by examiner

*Primary Examiner*—Jill Warden
*Assistant Examiner*—Lore Ramillano
(74) *Attorney, Agent, or Firm*—Harness, Dickey & Pierce, PLC

(57) ABSTRACT

In order to identify a marking which is arranged on a body and contains a marking substance with a specific property, the marking initially is scanned by use of radiation. The marking substance is then brought into contact with a detector substance having a specific property corresponding to the marking substance. A combination of the marking and detector substances which results because of the corresponding specific properties, exhibits fluorescent behavior. The marking is then scanned by use of the radiation in a second measurement, and identified by based upon the results of the two measurements.

15 Claims, 3 Drawing Sheets

METHOD AND DEVICE FOR IDENTIFYING A MARKER USING A DETECTOR SUBSTANCE

This application is the national phase under 35 U.S.C. § 371 of PCT International Application No. PCT/DE02/02691 which designated the United States of America and which claims priority on German Patent Application number DE 101 37 484.4 filed Aug. 3, 2001, the entire contents of which are hereby incorporated herein by reference.

FIELD OF THE INVENTION

The invention generally relates to a method and a device for identifying a marking which is arranged on a body and contains a marking substance with a specific property.

BACKGROUND OF THE INVENTION

A method and a device are known from WO 99/47702 A2. In this known method and this known device, the marking substance is brought into contact with a detector substance which has a specific property corresponding to the marking substance. The marking and detector substances are each configured as a nucleotide sequence, especially as a deoxyribonucleic acid (=DNA) or a peptide nucleic acid (=PNA). If the mutually matched nucleotide sequences are brought into contact with one another in a particular way, hybridization takes place. The nucleotide sequence of the detector substance is furthermore linked to at least one fluorophore molecule. Owing to measures which are additionally provided, this molecule does not develop its fluorescent property until after hybridization with the nucleotide sequence of the marking substance. By exposure to a light signal with a corresponding wavelength, a fluorescence reaction can then be induced which is employed to identify the marking.

WO 99/47702 A2 gives no indications about how the fluorescence reaction can be precisely detected. In fact, the received light radiation is made up of a first component, due to the fluorescence reaction of the hybridized marking, and a second component which results from reflection by the marking and, above all, by the marking background. Since only the fluorescent component of the marking identification can be used, it is necessary to separate this component. However, WO 99/47702 A2 provides no information about this. In the least favorable case, the two radiation components cannot be separated and no identification is possible.

A device, designed as a so-called fluorescence mirror scanner, for detecting an invisible marking which fluoresces in the near infrared wavelength is known from WO 97/50053 A2. In order to be able to separate the component coming from the background from the component caused by the fluorescence reaction in the received radiation, either tracking of the radiation source power or a special background material is provided in the disclosed device. The tracking is carried out so that the component caused by the background in the received radiation is kept constant. However, the power tracking entails a relatively complicated structure with a regulating unit. The other components used for constructing the fluorescence mirror scanner are also elaborate. The described device is furthermore not easy to transport and, in particular, it cannot be used as a hand-held instrument.

The same is true of another device for detecting an invisible fluorescent marking, which is described in U.S. Pat. No. 5,331,140. In order to separate the component caused by the fluorescence in the received radiation, the radiation used for excitation is modulated with two frequencies. An intermodulation component of these two frequencies is extracted from the electrical signal derived from the received radiation. The intermodulation product results from nonlinear behavior which is associated with the fluorescence reaction. The frequency modulation and separation of the intermodulation product entail outlay which is not inconsiderable. Other complicated components are furthermore used, for example the adjustable deflection mirror which directs the exciting radiation onto the various regions of the marking.

A device for identifying a marking which contains fluorescent material is described in JP 11-306276 A. The device is configured in the form of a hand-held instrument. An expensive optical filter is used for separating the background radiation and the fluorescent radiation in the received radiation. The device, just like all the others mentioned above, is furthermore suitable only for the detection of a marking which already fluoresces before the start of the measurement.

SUMMARY OF THE INVENTION

It is therefore an object of an embodiment of the invention to provide a method and a device for identifying a marking which is arranged on a body and contains a marking substance with a specific property, which function simply and rapidly and can be constructed without elaborate components. In particular, it should possible to produce the device in the form of a portable hand-held instrument.

The method according to an embodiment of the invention for identifying a marking which is arranged on a body and contains a marking substance with a specific property is a method in which a) the marking is scanned by means of radiation in a first measurement and a reference is determined therefrom, b) the marking substance is brought into contact with a detector substance having a specific property corresponding to the marking substance, so that a combination of the marking and detector substances which results because of the corresponding specific properties exhibits fluorescent behavior, c) the marking is scanned by use of the radiation in a second measurement, and d) the marking is identified by use of the reference and the result of the second measurement.

The device according to an embodiment of the invention for identifying a marking which is arranged on a body and contains a marking substance with a specific property is a device which comprises at least a) a scanning unit for measuring the marking by means of radiation, b) a dosing unit which can be filled with a detector substance and is designed to bring the detector substance into contact with the marking substance, wherein the detector substance has a specific property corresponding to the marking substance, and a combination of the marking and detector substances which results because of the corresponding specific properties exhibits fluorescent behavior, and c) a control and evaluation unit, wherein the scanning unit, the dosing unit and the control and evaluation unit are designed for sequentially d) carrying out a first measurement of the marking and determination, derived therefrom, of a reference, e) bringing the marking substance and the detector substance into contact, f) carrying out a second measurement of the marking, and g) carrying out identification of the marking with the aid of the reference and the result of the second measurement.

An embodiment of the invention is in this case based on the discovery that separation of the background-radiation component from the fluorescent radiation is possible with simple means owing to the prior first measurement to record a reference for the background radiation. This is because after the substance has been applied, the radiation received in the scope of the second measurement also contains a fluorescent-radiation component, owing to the fluorescent behavior of the combination of the marker and detector substances, besides the background-radiation component. The result of the first (reference) measurement is then used to eliminate the background-radiation component from the result of the second measurement, so that essentially only the component of interest remains, which has been caused by the fluorescence reaction of the marking. In this way, it is possible to identify the marking.

Before combination with the detector substance, the marking substance advantageously exhibits no fluorescent behavior of its own, or no such notable fluorescent behavior. In any event, its own fluorescence is not significant compared with that which is present after combination with the detector substance. Just like the other background, however, the marking substance may exhibit minor fluorescence, for example natural fluorescence. This minor fluorescence of the marking and the background, which may be present, will nevertheless be recorded using the reference measurement and can be taken into account at the same time when evaluating the second measurement.

Determination of a reference for the background radiation is possible, in particular, because the marking exhibits no fluorescent behavior, or only insubstantial fluorescent behavior, before the detector substance is applied. This particularly advantageous way of determining a reference for the background radiation is not available in the methods and devices of the prior art, since they operate with markings which already exhibit fluorescent behavior from the start.

By virtue of the sequential measures of the reference measurement, delivery of the detector substance, and the second measurement, the marking can be identified in a particularly simple way with the method according to the invention and the device according to an embodiment of the invention. Determination of the reference may be carried out with the same components as are provided anyway for the actual measurement. The reference measurement is in this case taken into account, in particular, at the level of the electrical signals derived from the received radiation. This is advantageously done after prior digitization inside an electronic computer unit which, for example, is a component of the control and evaluation unit. Very rapid identification of the marking is therefore possible despite the additional reference measurement, and in spite of the reference which has been determined being taken into account during evaluation of the second measurement.

When advantages are explicitly indicated below only for a method configuration or a device configuration, these also apply to the respectively corresponding device or method configuration.

A configuration in which the first measurement (=reference measurement), the step in which the detector substance is brought into contact with the marking substance, and the second measurement are carried out in chronological succession is favorable. This ensures that the ambient conditions and, in particular, the background behavior do not change between the reference measurement and the second measurement. A better identification result is therefore obtained. Very rapid identification is furthermore achieved by this. The application of the detector substance, which takes place immediately before the second measurement, furthermore substantially precludes decomposition of the combination of the marking and detector substances happening before the second measurement is carried out.

A further embodiment, in which a device used for the identification is moved across the marking, is advantageous. The movement may, in particular, take place manually. It is furthermore advantageously also possible for the device being used to be moved across the marking in a forward direction and subsequently in a backward direction. The movement across the marking obviates the elaborate operation of scanning the marking by use of the radiation, which is customarily employed in the prior art. Owing to the fact that the entire device is moved, the radiation emitted for scanning the marking picks up all the relevant parts of the marking, without a special operation being needed for this. This provides a particularly simple configuration of the device and the method. It is furthermore favorable for the device to be in direct contact with the marking during the movement across the marking. This prevents fluctuations in the result due to a varying distance from the marking, even if the movement is being performed by hand. Direct contact between the device being used and the marking furthermore makes it possible to reduce, or even completely prevent, the introduction of undesired scattered radiation.

In a further advantageous embodiment, the position is recorded during the movement across the marking and is also taken into account during the evaluation. This makes it possible to take into account fluctuations in the movement speed, which might otherwise lead to vitiation of the results.

An embodiment in which the movement across the marking takes place by rolling a roller across the marking is furthermore favorable. More favorably, this roller is at the same time used for delivery of the detector substance to the marking, and therefore to the marking substance. The roller furthermore serves to keep the distance between the marking and the scanning unit constant, so that a high measurement accuracy is achieved. The roller hence fulfills a plurality of functions simultaneously.

In another preferred variant, the result of the first measurement is also employed for evaluating the fluorescent behavior of the marking, in addition to determining the reference. This evaluation hence provides information about whether the marking already exhibits significant fluorescence before the detector substance is delivered. If so, this can be an important indication of an attempted forgery or of an unauthorized attempt at identification.

A further configuration is distinguished by the fact that the radiation directed at the marking in order to excite the fluorescence exists as a radiation pattern. Possible patterns are in this case a line pattern or a point pattern, advantageously with an elongate outline in each case. This is favorable, in particular, in the case of a device which is designed as a hand-held instrument. Manual movement of the device across the marking does not in general take place exactly uniformly. When the fluorescent radiation is excited by use of a light pattern with a sizeable local extent, which is in particular also elongate, fluctuations during the movement across the marking are not important. However, the excitation provided in the prior art by use of a single point of light, which is furthermore very small, does not have this advantage.

BRIEF DESCRIPTION OF THE DRAWINGS

Preferred exemplary embodiments will now be explained in more detail with reference to the drawings. For clarity, the drawings are not true to scale, and certain features are represented only schematically. Specifically.

Parts which correspond to one another are provided with the same reference numerals in FIGS. 1 to 6.

DETAILED DESCRIPTION OF THE PREFERRED EMBODIMENTS

Figure 1:
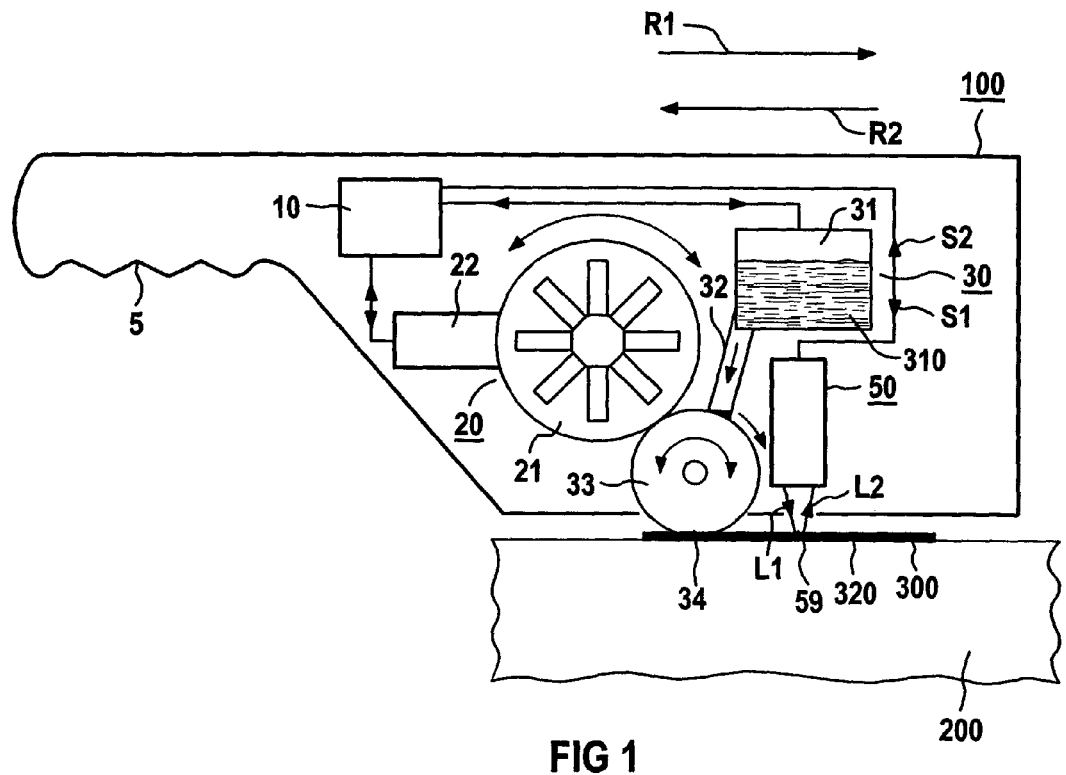
FIG. 1 shows a device in the form of a hand-held instrument for identifying a marking.

FIG. 1 schematically represents a device 100 for identifying a marking 300 on a body 200. The body 200 may have any configuration, for example packaging, a document or another product, which is intended to be labeled. The marking 300 contains a marking substance 320, which has a specific property. The marking substance 320 is configured as a nucleotide sequence, for example as deoxyribonucleic acid (=DNA) or as peptide nucleic acid (=PNA), in the exemplary embodiment which is shown. In particular, the marking 300 is invisible to the human eye. The effect achieved by this is that a chance observer cannot gain knowledge of the marking. This is of benefit, inter alia, in the field of protection against product piracy.

The device 100 shown in FIG. 1 is designed as a hand-held instrument, in order to allow most simple, rapid and flexibly usable identification of the marking 300, even if the marking 300 is located in a very remote and sometimes even inaccessible position.

The marking 300 formed by the marking substance 320 cannot initially be detected, even by optical scanning with any wavelength whatsoever, without further processing. To identify the marking 300, the device 100 therefore contains a dosing unit 30, by use of which a detector substance 310 can be delivered to the marking 300 and brought into contact with the marking substance 320. The detector substance 310 likewise has a specific property, which corresponds precisely to that of the marking substance 310. The detector substance 310 is also a nucleotide sequence, PNA in the present case. If the marking and detector substances 320 and 310, respectively, are correctly selected with mutually corresponding specific properties, combination (=hybridization) of the two nucleotide sequences takes place after the two substances 310 and 320 have been brought into contact with one another. It is, in particular, advantageous to use PNA for the substances 310 and 320 because a particularly stable and heat-resistant combination is then obtained after the hybridization.

The detector substance 310 additionally contains a fluorophore component, although this is deactivated by an additional measure when the PNA of the detector substance 310 is in the unhybridized state. Thus, it does not exhibit any fluorescent behavior. After hybridization with the PNA of the marking substance 320, the deactivation of the fluorophore element is removed and it exhibits its fluorescent behavior, which can be optically excited and detected. Various embodiments of the nucleotide sequences which are used, as well as the binding of a fluorophore molecule to the detector substance 310, are indicated in WO 99/47702 A2. In the example shown in FIG. 1, fluorescein or Cy 5 is used as the fluorophore element. Fluorescein can in this case be fluorescently excited by light radiation in the wavelength range around 470 nm, whereas Cy 5 can be fluorescently excited by way of light radiation in the wavelength range around 640 nm. The fluorescent radiation emitted by Cy 5 then lies in a wavelength range around 670 nm.

For the identification, the device 100 is moved manually across the marking 300. The detector substance 310 is applied to the marking 300 during this movement. The dosing unit 30 provided therefor contains a container 31, a feed 32 and a roller 33 for this purpose. In the container 31, there is a store of the detector substance 310, which is present in aqueous solution in the exemplary embodiment being shown. Other embodiments are nevertheless also conceivable. Via the feed 32, the detector substance 310 reaches the roller 33, which rotates during the movement of the device 100 across the marking 300, and hence distributes the detector substance 310 uniformly on the marking 300. The detector substance 310 may also in principle be delivered to the marking 300 in a different fashion. One conceivable alternative resides in using a pipette, whose delivery capacity may optionally be controllable.

The roller 33 used in the exemplary embodiment of FIG. 1 for delivering the detector substance 310 is in immediate contact with the marking 300. This has the advantage that the other components of the device 100 are respectively located at about the same distance from the marking 300 during the identification process. Practically constant conditions are therefore obtained for optically scanning the marking 300 throughout the identification process. The distance between the marking 300 and the other components of the device 100 can be adjusted with the aid of the bearings of the roller 33 in the device 100. A distance which is as small as possible is particularly advantageous in this case, in order to reduce undesired introduction of scattered light in conjunction with the optical scanning.

The device 100 has a handle 5, by which it can be moved to and fro across the marking 300 in a forward direction R1 and a backward direction R2. A transmission light signal L1 is directed onto the marking 300 by means of a scanning unit 50. A reception light signal L2 scattered back therefrom is received by the scanning unit 50 and forwarded after optoelectronic conversion as a reception signal S2 to a control and evaluation unit 10. Besides the scanning unit 50, the control and evaluation unit 10 also controls the dosing unit 30 as well as a positioning unit 20.

The positioning unit 20 records the position of the device 100 during the movement taking place along the marking, and forwards a measurement value of the position to the control and evaluation unit 20. The positioning unit 20 contains a positioning disk 21 for this purpose, which is in contact with the roller 33. Rotation of the roller 33 also causes a corresponding rotation of the positioning disk 21, and this is in turn recorded by a position-recording unit 22 and forwarded to the control and evaluation unit 10.

A scanning position 59 determined by the scanning unit 50 is located, in relation to a forward direction R1, in front of a delivery position 34 which is determined by the dosing unit 30 and at which the detector substance 310 leaves the dosing unit 30 in order to enter into contact with the marking substance 320. The delivery position 34 is determined by the roller 33 in the exemplary embodiment being shown. Owing to this particular advantageous arrangement of the scanning position 59 and the delivery position 34, a first scanning measurement can be carried out during movement in the forward direction R1, before the marking 300 is actually hybridized and exhibits its significant fluorescent behavior. The result obtained on the basis of this first scanning measurement is saved as a reference in the control and evaluation unit 10. The reference essentially describes the scattering behavior of the background of the marking 300 when it is exposed to the transmission light signal L1. Any minor natural fluorescence of the background and the marking 300 which may be present will also be recorded as well by the reference, and taken into account at the same time during the subsequent evaluation of further measurement results.

After the device 100 has been moved across the marking 300 completely in the forward direction R1, the reference measurement and the application of the detector substance 310 onto the marking 300 are concluded. During the movement which then takes place in the backward direction R2, a second scanning measurement is carried out which, moreover, this time leads to excitation of the now hybridized and fluorescent marking 300. In contrast to the first measurement, the reception light signal L2 now also contains, besides the component which is determined by the background, a further component which is determined by the significant fluorescence of the marking 300. Separation of these two components is normally quite complex. Elaborate mechanisms are therefore often provided in known devices for the identification of fluorescent markings. The device 100, however, copes without complicated components since a reference value for the background-radiation component has already been determined in the first measurement. Separation of the two components of the reception light signal L2 can therefore be carried out straightforwardly in the control and evaluation unit 10. The desired identification of the marking 300 takes place by use of the fluorescent component extracted in the control and evaluation unit 10.

Figure 2:
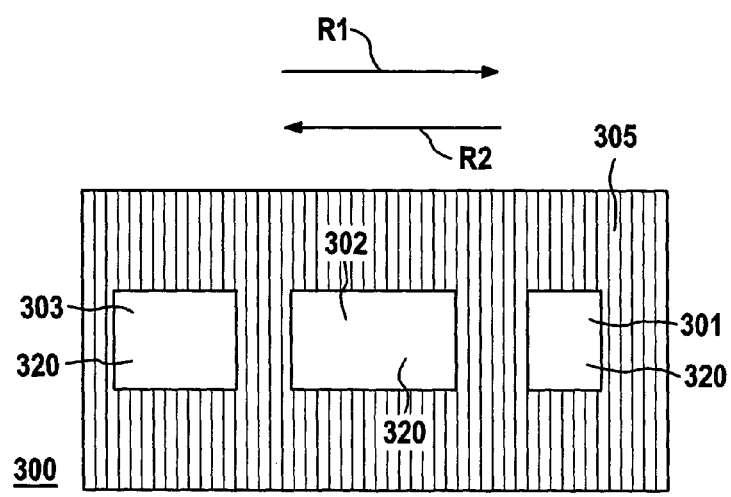
FIG. 2 shows a marking on a background pattern.

FIG. 2 represents a plan view of a possible embodiment of the marking 300. The marking 300 has in principle the shape of a standard bar code which, in the example being shown, is made up of three marking parts 301, 302 and 303 in all. The marking substance 320 is also found in the region of these marking parts 301, 302 and 303. After hybridization with the detector substance 310, significant fluorescent behavior can hence be observed in precisely these regions.

The example of the marking 300 shown in FIG. 2 additionally contains a reference background 305, which causes a characteristic background component in the reception light signal L2, with the aid of which position determination can be carried out in the control and evaluation unit 10. A special positioning unit 20 would not then be required for this. The reference background 305 consists of a parallel line pattern, which appears as a specific periodicity in the component of the reception light signal L2 determined by the background. Position determination can hence be carried out both by use of the positioning unit 20 and by use of the reference background 305 during manual movement of the device 100 across the marking 300. With the aid of the position data obtained in this way, it is possible to derive additional information, for example about the size and position of the marking parts 301, 302 and 303, and also take this into account in the evaluation, if so desired.

Figure 3:
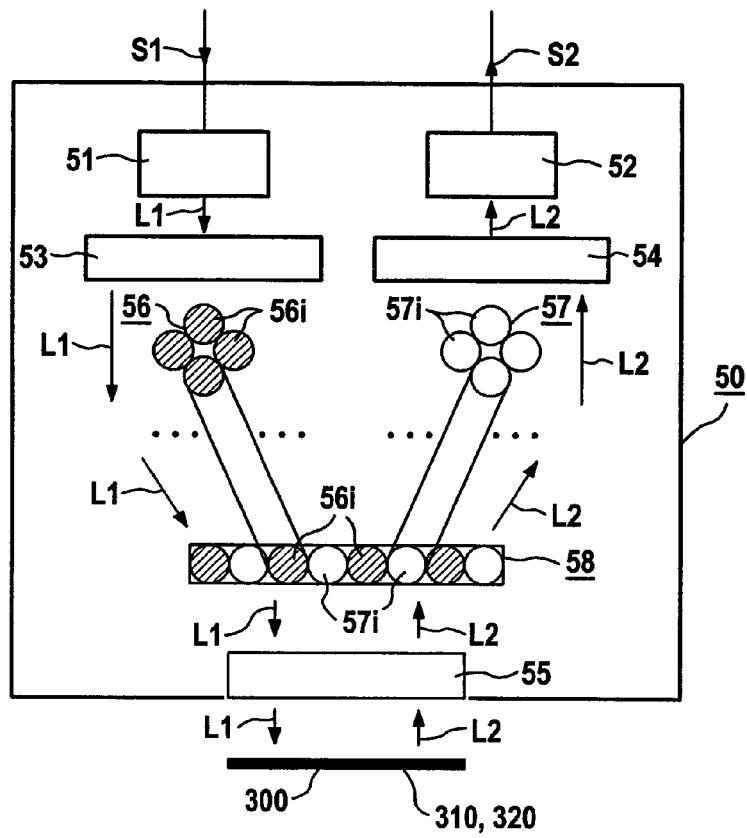
FIG. 3 shows a scanning unit used in the device according to FIG. 1, FIGS. 4 and 5 show a waveguide arrangement of the scanning unit of FIG. 4 in side view.

The scanning unit 50 is represented in more detail in FIG. 3. This is an embodiment with a waveguide structure. A free-beam structure is also possible in principle.

The scanning unit 50 includes a light source 51 which, after having received a control signal S1 from the control and evaluation unit 10, starts a measurement by emitting the transmission light signal L1. The transmission light signal L1 is sent via a first lens 53 into a transmission bundle 56 including a plurality of transmission optical waveguides 56$i$ and, after having traveled through the transmission optical waveguides 56$i$, is directed onto the marking 300 via a further lens 55 in the form of a bar lens.

The marking 300 has fluorescent behavior, that is to say there is hybridization between the marking and detection substances 310, 320. The transmission light signal L1 fluorescently excites the fluorophore molecules. The excited fluorescent radiation forms a second component in the reception light signal L2, which is additional to the first component caused by a simple reflection and/or scattering of the transmission light signal L1 by the marking 300 and is fed into the reception optical waveguides 57$i$ via the bar lens 55.

The reception light signal L2 travels through the reception optical waveguides 57$i$ in the direction opposite to the direction in which the transmission light signal L1 travels through the transmission optical waveguides 56$i$. At the other end from the marking 300, the reception optical waveguides 57$i$ are combined to form a circular or elliptical reception bundle 57. The transmission bundle 56 also has such a circular or elliptical circumference at the end facing the light source 51. This bundle shape facilitates input or output of light into the bundle 56 and out of the bundle 57, respectively. In the case of the reception bundle 57, the emerging reception light signal L2 is focused onto the sensitive detector face of a photodetector 52 by means of a further lens 54.

If need be, an optical filter (not shown in FIG. 3) may also be arranged between the lens 54 and the photodetector 52, in order to further reduce any per se undesired light input into the photodetector 52 possibly caused by ambient light or reflected components of the transmission light signal L1. The reception light signal L2 is converted into the electrical reception signal S2 in the photodetector 52.

Figure 4:
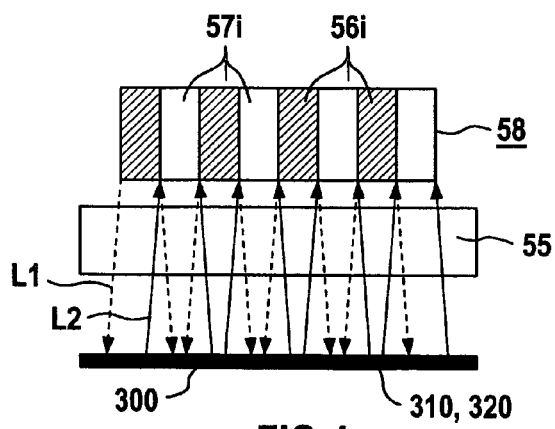
Figure 5:
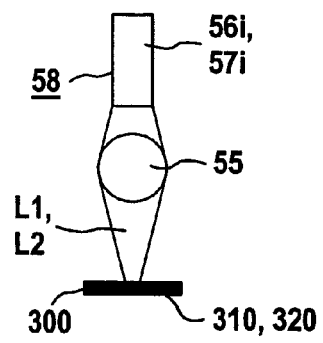

The optical waveguide structure allows simple separation of the transmission and reception light signals L1 and L2. Compared with an optical free-beam arrangement, the version with the optical waveguides 56$i$ and 57$i$ can furthermore be made much smaller. It is also more flexible in relation to the geometrical configurations which are possible. A further advantage of the optical waveguide structure is that an elongate scanning pattern can be generated in a straightforward way on the marking 300. For this purpose, the transmission bundle 56 and reception bundle 57 separated from one another at the positions of the light source 51 and the photodetector 52 are combined to form a single transmission/reception bundle 58 at the position of the marking 300. In the reception bundle 58, the transmission and reception optical waveguides 56$i$ and 57$i$ are arranged next to one another in alternation. This provides an elongate exit and entry face respectively for the transmission light signal L1 and for the reception light signal L2. This elongate face is also projected onto the marking 300 as an elongate scanning pattern by the bar lens 55. The detail of the scanning unit 50 with the combined transmission/reception bundle 58 comprising the transmission and reception optical waveguides 56$i$ and 57$i$, as well as the focusing bar lens 55, is represented in FIGS. 4 and 5 in the two side views.

The elongate shape of the scanning pattern is advantageous especially in a device 100 designed as a hand-held instrument. This is because the manual movement of the device 100 necessarily leads to certain fluctuations, so that a small point-light scanning pattern could inadvertently miss the region of the marking parts 301, 302 and 303 to be detected, owing to this irregular manual movement. This risk does not exist in the case of an elongate scanning pattern. Better and more reliable results can therefore be achieved by this simple measure.

Figure 6:
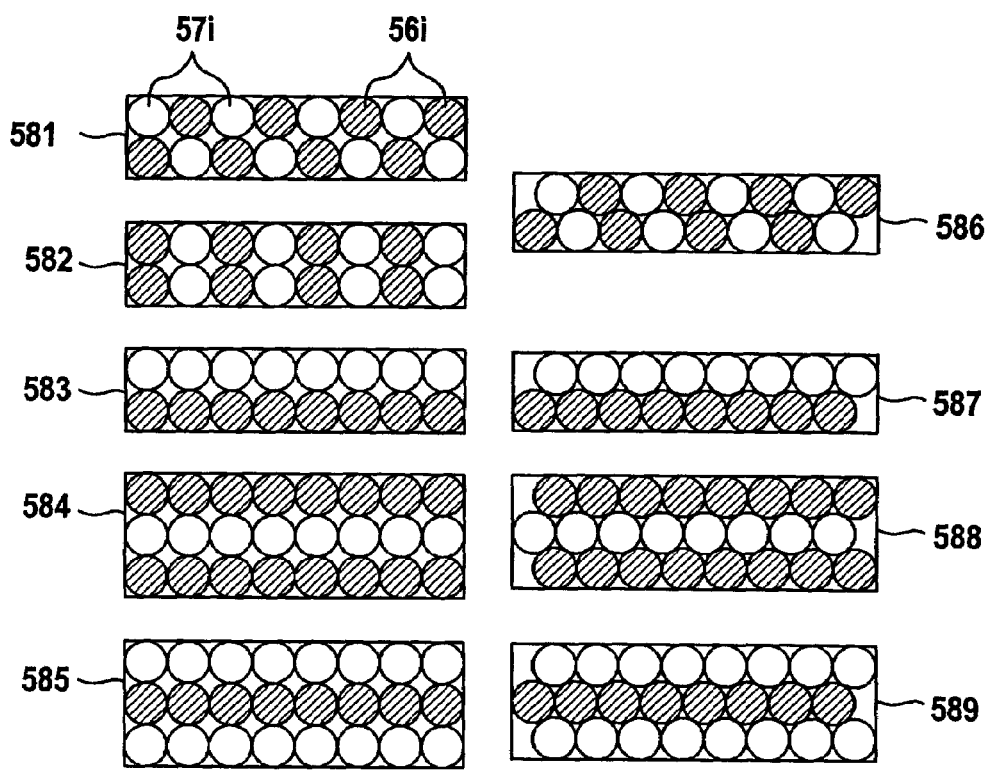
FIG. 6 shows arrangements of input and output waveguides in the scanning unit according to FIG. 3.

The transmission and reception optical waveguides 56*i* and 57*i* may also be arranged next to one another in a fashion other than that represented in FIG. 3. Alternative embodiments of transmission/reception bundles are represented in FIG. 6 and labeled with the reference numerals 581 to 589.

In a further embodiment (not shown), at least two different types of fluorophore molecules, each with a different excitation and fluorescence wavelength, are provided in the detector substance 320. The security against undesired identification of the marking 300 can hereby be increased, as can the accuracy during intentional and allowed identification. In this case, the transmission and reception optical waveguides 56*i* and 57*i* are advantageously subdivided into further sub-bundles, each of which carries a light component with one of the wavelengths being used. Each excitation and fluorescent wavelength is then assigned to one of the sub-bundles.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A method for identifying a marking which is arranged on a body and contains a marking substance with a specific property, comprising:
   scanning the marking by use of radiation in a first measurement and determining a reference therefrom;
   bringing the marking substance into contact with a detector substance having a specific property corresponding to the marking substance, so that a combination of the marking and detector substances exhibits fluorescent behavior;
   scanning the marking by use of the radiation in a second measurement; and
   identifying the marking by using the reference and a result of the second measurement, and wherein
   scanning the marking by use of radiation in a first measurement, bringing the marking substance into contact with a detector substance, and scanning the marking by use of the radiation in a second measurement is carried out in chronological succession.

2. The method as claimed in claim 1, wherein bringing a device in contact with the marking includes moving the device across the marking for the first and second measurement.

3. The method as claimed in claim 1, wherein bringing a device in contact with the marking includes moving the device across the marking for the first and second measurement.

4. The method as claimed in claim 3, wherein the device is moved manually.

5. The method as claimed in claim 3, wherein the device is moved across the marking, first in a first direction and then in a second direction opposite the first direction.

6. The method as claimed in claim 5, wherein the first measurement is carried out during the movement in the first direction.

7. The method as claimed in claim 6, wherein the second measurement is carried out during the movement in the second direction.

8. The method as claimed in claim 5, wherein the contact is brought about during the movement in the first direction.

9. The method as claimed in claim 8, wherein the second measurement is carried out during the movement in the second direction.

10. The method as claimed in claim 5, wherein the second measurement is carried out during the movement in the second direction.

11. The method as claimed in claim 3, wherein the device is brought into direct contact with the marking during the movement.

12. The method as claimed in claim 3, wherein a position of the device is recorded during the movement.

13. The method as claimed in claim 3, wherein a first and a second nucleotide sequence are respectively used as the detector substance and the marking substance.

14. The method as claimed in one claim 3, wherein a detector substance having a fluorophore component is used.

15. The method as claimed in claim 1, wherein the fluorescent behavior of the marking is evaluated with the aid of the first measurement before the marking substance is brought into contact with the detector substance.

* * * * *